(12) United States Patent
Proksa et al.

(10) Patent No.: US 11,026,643 B2
(45) Date of Patent: Jun. 8, 2021

(54) INTERFEROMETER GRATING SUPPORT FOR GRATING-BASED X-RAY IMAGING AND/OR A SUPPORT BRACKET THEREFOR

(71) Applicant: KONINKLIJKE PHILIPS N.V., Eindhoven (NL)

(72) Inventors: Roland Proksa, Neu Wulmstorf (DE); Thomas Koehler, Norderstedt (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 55 days.

(21) Appl. No.: 16/463,857

(22) PCT Filed: Nov. 30, 2017

(86) PCT No.: PCT/EP2017/080889
§ 371 (c)(1),
(2) Date: May 24, 2019

(87) PCT Pub. No.: WO2018/104132
PCT Pub. Date: Jun. 14, 2018

(65) Prior Publication Data
US 2019/0336086 A1 Nov. 7, 2019

Related U.S. Application Data

(60) Provisional application No. 62/430,402, filed on Dec. 6, 2016.

(51) Int. Cl.
*A61B 6/00* (2006.01)
*A61B 6/03* (2006.01)
*G21K 1/06* (2006.01)

(52) U.S. Cl.
CPC ............ *A61B 6/035* (2013.01); *A61B 6/4035* (2013.01); *A61B 6/484* (2013.01); *G21K 1/06* (2013.01)

(58) Field of Classification Search
CPC .. A61B 6/00; A61B 6/03; A61B 6/035; A61B 6/484; A61B 6/4035; A61B 6/06;
(Continued)

(56) References Cited

U.S. PATENT DOCUMENTS 5,812,629 A * 9/1998 Clauser .................. A61B 6/466
378/62
7,639,786 B2 12/2009 Baumann et al.
(Continued)

OTHER PUBLICATIONS

PCT International Search Report, International application No. PCT/EP2017/080889, dated Apr. 13, 2018.
(Continued)

*Primary Examiner* — Jurie Yun
(74) *Attorney, Agent, or Firm* — Larry Liberchuk

(57) ABSTRACT

An interferometer grating support (118) of an imaging system (100) configured for grating-based x-ray imaging includes at least two elongate supports (302) separated from each other by a non-zero distance, wherein the at least two elongate supports have a first end (312) and a second end (316). The grating support further includes a first arc shaped grating (202) affixed to the first end and a second arc shaped grating (204) affixed to a second end (316). A non-transitory computer readable medium is configured with computer executable instructions which when executed by a processor of a computer cause the processor to: move a grating support, which supports G0 and G1 gratings of an interferometer and a bowtie filter, into a region between a low energy photon filter and a beam collimator, which are between a radiation source and an examination region, for a grating-based x-ray imaging scan.

21 Claims, 7 Drawing Sheets

(58) Field of Classification Search
CPC ........... A61B 6/44; A61B 6/4417; A61B 6/54; G21K 1/06; G01J 2003/1204; G01J 2003/1226; G01J 2003/1213; G01J 2003/1221

See application file for complete search history.

(56) References Cited

U.S. PATENT DOCUMENTS

| | | |
|---|---|---|
| 9,084,528 B2 | 7/2015 | Geller et al. |
| 2007/0183559 A1 | 8/2007 | Hempel |
| 2010/0091936 A1 | 4/2010 | David et al. |
| 2014/0037059 A1 | 2/2014 | Suft |
| 2014/0226785 A1 | 8/2014 | Stutman et al. |
| 2015/0023465 A1 | 1/2015 | Sato |
| 2015/0071402 A1 | 3/2015 | Nanda |
| 2015/0117598 A1 | 4/2015 | Proksa |
| 2015/0124927 A1 | 5/2015 | Koehler et al. |
| 2015/0294749 A1 | 10/2015 | Gorelick |

OTHER PUBLICATIONS

Donath T. et al, "Inverse Geometry for Grating-Based X-Ray Phase-Contrast Imaging", Journal of Applied Physics 106, pp. 054703-1-054703-7, Oct. 2009.

\* cited by examiner

… (1)

INTERFEROMETER GRATING SUPPORT FOR GRATING-BASED X-RAY IMAGING AND/OR A SUPPORT BRACKET THEREFOR

TECHNICAL FIELD

The following generally relates to grating-based x-ray imaging, which, herein, refers to grating-based phase contrast imaging, which provides three contrasts in a scanned object—attenuation, phase, and dark-field, and thus can also be referred as grating-based phase contrast and/or dark-field contrast imaging. More particularly, the following relates to an interferometer grating support for grating-based x-ray imaging and/or a support bracket for the interferometer grating support, and is described with particular application to computed tomography (CT).

BACKGROUND

In conventional CT imaging, contrast is obtained through the differences in the absorption cross-section of the constituents of the scanned object. This yields good results where highly absorbing structures such as bones are embedded in a matrix of relatively weakly absorbing material, for example the surrounding tissue of the human body. However, in cases where different forms of tissue with similar absorption cross-sections are under investigation (e.g., mammography or angiography), the X-ray absorption contrast is relatively poor. Consequently, differentiating pathologic from non-pathologic tissue in an absorption radiograph remains difficult for certain tissue compositions. Grating-based x-ray imaging overcomes this limitation. Grating-based x-ray imaging utilizes X-ray gratings, which allow acquisition of X-ray images in phase contrast, which provides additional information about the scanned object. Another advantage of grating-based x-ray imaging is that it is also sensitive to small-angle scattering, often called dark-field contrast. Dark-field contrast is generated by small structures like alveoli in the lung or the fine sponge-type structure in bones.

Grating-based x-ray imaging uses three gratings, a source grating close to the X-ray source, an absorber grating close to the detector, and a phase or absorber grating disposed depending on whether configured with conventional, inverse, or symmetric geometry. Certain distances between gratings, grating shapes, grating locations, etc. need to be established and maintained for imaging. Unfortunately, this may be difficult. For example, there is a limited amount of free space in which the gratings can be added. Furthermore, in addition to the gratings, other X-ray beam conditioning components are between the X-ray tube output window and the examination area. This includes a low energy filter, a bow-tie shaped attenuator, and a beam collimator. Hence, these other components must also be considered and may further limit the space for the gratings. In view of at least the foregoing, there is an unresolved need for an approach to facilitate meeting and/or maintaining the requirements for the gratings for grating-based x-ray imaging.

SUMMARY

Aspects described herein address the above-referenced problems and others.

In one aspect, an interferometer grating support of an imaging system configured for grating-based x-ray imaging includes at least two elongate supports separated from each other by a non-zero distance. The grating support further includes a first arc shaped grating affixed to a first end of the at least two elongate supports. The grating support further includes a second arc shaped grating affixed to a second end of the at least two elongate supports.

In another aspect, an imaging system configured for grating-based x-ray imaging includes a gantry, a radiation source, a detector array disposed across an examination region from the radiation source; a grating support disposed between the radiation source and the examination region, and an interferometer. The interferometer includes a source grating G0, a phase or absorber grating G1, and absorber grating G2. The grating support supports gratings G0 and G1. The grating G2 is disposed between the examination region and the detector array.

In another aspect, a non-transitory computer readable medium is configured with computer executable instructions which when executed by a processor of a computer cause the processor to: move a grating support, which supports G0 and G1 gratings of an interferometer and a bowtie filter, into a region between a low energy photon filter and a beam collimator, which are between a radiation source and an examination region, for a grating-based x-ray imaging scan.

Those skilled in the art will recognize still other aspects of the present application upon reading and understanding the attached description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
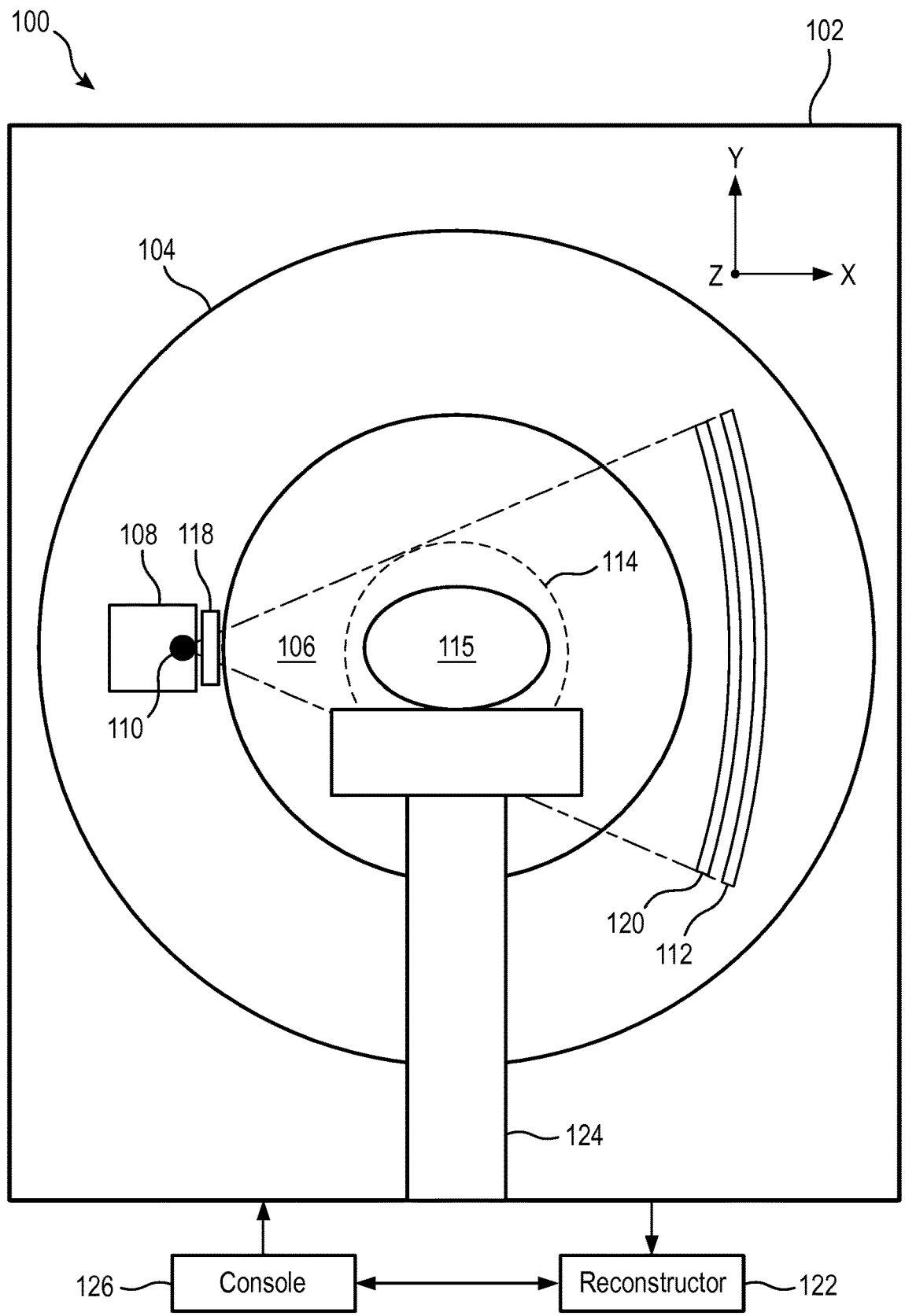
FIG. 1 schematically illustrates an example imaging system including an interferometer grating support.

FIG. 1 schematically illustrates an imaging system 100, such as a CT scanner, which is configured for grating-based x-ray imaging. The imaging system 100 includes a generally stationary gantry 102, which houses a rotating gantry 104 that is rotatably supported by the stationary gantry 102 via a bearing or the like and that rotates around an examination region 106 about a z-axis. A radiation source 108 (e.g., an X-ray tube), which produces a focal spot 110, is rotatably supported by the rotating gantry 104, rotates with the rotating gantry 104, and emits radiation (via the focal spot 110) that traverse the examination region 106. A radiation sensitive detector array 112 is located opposite the radiation source 108 across the examination region 106. The radiation sensitive detector array 112 detects radiation traversing a field of view 114 and an object 115 therein and generates a signal (projection data) indicative thereof.

Figure 2:
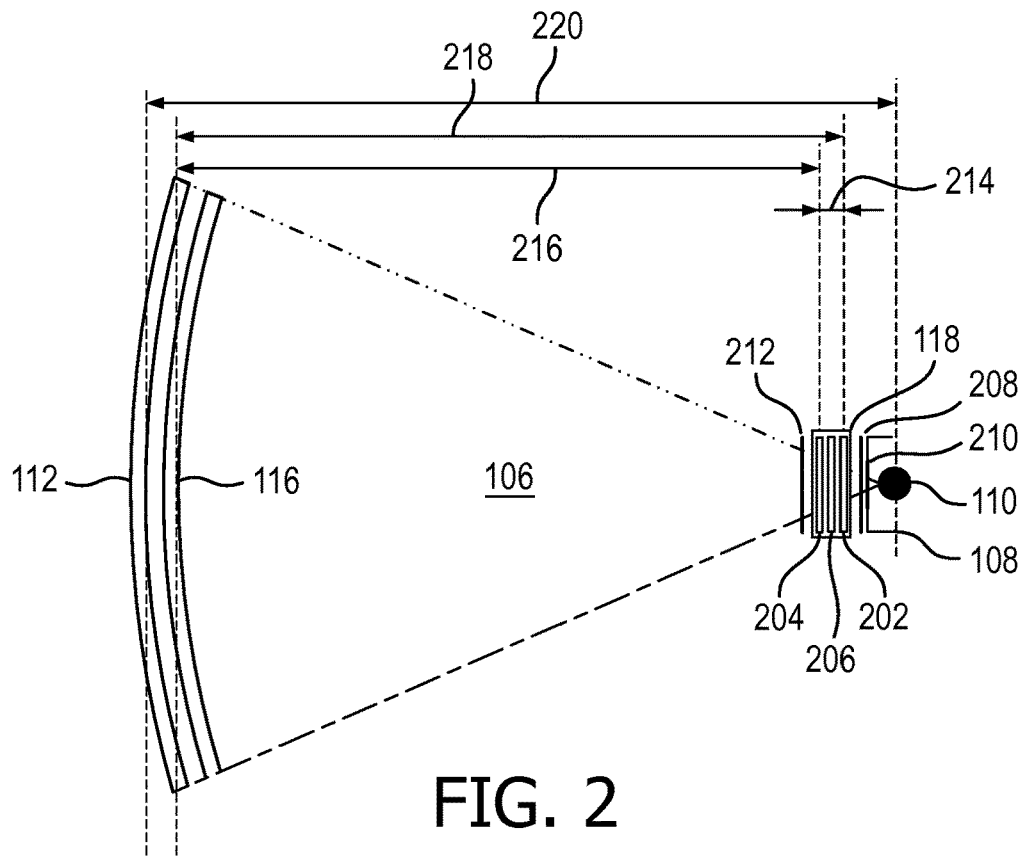
FIG. 2 schematically illustrates example of relative locations of the gratings of the interferometer in the system.

An X-ray imaging interferometer is also rotatably supported by the rotating gantry 104 and rotates with the rotating gantry 104. The X-ray imaging interferometer includes three gratings. In FIG. 1, an interferometer grating support ("grating support") 118 supports two of the gratings, and a third grating, an absorber grating (G2) 120, is located between the examination region 106 and the radiation sensitive detector array 112. FIG. 2 shows an example in which the grating support 118 supports a source grating (G0) 202 and a phase or absorber grating (G1) 204. As described in greater detail below, the grating support 118 is configured so that the space between the G0 grating 202 and the G1 grating 204 is sufficient for high phase-contrast and dark-field sensitivity, the relative position of the G0 grating 202 to the G1 grating 204 is precise, and the placement has suitable geometrical accuracy and stability, including while rotating. Furthermore, the grating support 118 allows for a geometrically calibration G0 and G1 (e.g., a rotation between the gratings) outside the system 100, e.g., in a calibration and/or other step.

Continuing with FIG. 2, disposed between the G0 grating 202 and the G1 grating 204 is a conventional bow-tie filter 206. This example also shows a low x-ray energy photon filter 208 between an X-ray window 210 of the source 108 and the grating support 118, and an x-ray beam collimator 212 between the grating support 118 and the examination region 106. As described in greater detail below, in one non-limiting embodiment, a support bracket supports the grating support 118 and the low energy photon filter 208 and/or the beam collimator 212. Additionally or alternatively, as described in greater detail below, the support bracket also supports one or more other beam conditioning components, which is/are alternatively positioned (in alternative to the grating support 118) between the low energy photon filter 208 and the beam collimator 212, via electro-mechanical control.

FIG. 2 also shows the relative geometry of the gratings. In this example, a distance 214 between the G0 grating 202 and the G1 grating 204 is less than a distance 216 between the G1 grating 204 and the G2 grating 116. That is, the G1 grating 204 is closer to the G0 grating 202 than the G2 grating 116. A distance 218 is between the G0 grating 202 and the G2 grating 116. A distance 220 is a distance between the focal spot 110 and the detector array 112. This configuration is considered inverse geometry. Inverse, conventional and symmetric configurations are discussed in Donath et al., "Inverse geometry for grating-based x-ray phase-contrast imaging," Journal of Applied Physics," 106, 054703, 2009. An example of suitable distances and pitches is described in patent application publication US 2015/0117598 A1, filed Dec. 4, 2014, and entitled "Grating-Based Differential Phase Contrast Imaging," which is incorporated herein by reference in its entirety.

Returning to FIG. 1, a reconstructor 122 reconstructs the signals generated by the array 112. In one instance, the reconstructor 122 is configured to generate a conventional CT image. In another instance, the reconstructor 122 is configured to generate a dark field image. In another instance, the reconstructor 122 is configured to generate phase images. In yet another instance, the reconstructor 122 is configured to generate phase images and a dark field image. In another instance, the reconstructor 122 is configured to generate a conventional CT image and dark field image. In another instance, the reconstructor 122 is configured to generate a conventional CT image and phase images. In another instance, the reconstructor 122 is configured to generate a conventional CT image, a dark field image and phase images.

An example of reconstruction of conventional CT, dark field and/or phase images is described in patent application publication US 2015/0117598 A1, filed Dec. 4, 2014, and entitled "Grating-Based Differential Phase Contrast Imaging," which is incorporated herein by reference in its entirety. Another example of x-ray imaging is described in U.S. Pat. No. 9,084,528 B2, filed Dec. 3, 2010, and entitled "Phase Contrast Imaging," which is incorporated herein by reference in its entirety. Another example of dark field imaging is described in patent application publication US 2015/0124927 A1, filed May 13, 2013, and entitled "Dark field computed tomography imaging," which is incorporated herein by reference in its entirety.

A subject support 124, such as a couch, supports the object 115 in the field of view 114 before, during and/or after scanning a subject or object. A general-purpose computing system or computer serves as an operator console 126. The console 126 includes a human readable output device such as a monitor and an input device such as a keyboard, mouse, etc. Software resident on the console 126 allows the operator to interact with and/or operate the imaging system 100 via a graphical user interface (GUI) or otherwise. This includes selecting an imaging protocol, e.g., a grating-based x-ray imaging protocol, initiating scanning, etc. In one instance, as described in greater detail below, the console 126 sends a signal which cause the grating support 118 and the G2 grating 120 to move into position for a grating-based x-ray imaging scan or a position for a conventional CT scan.

Figure 3:
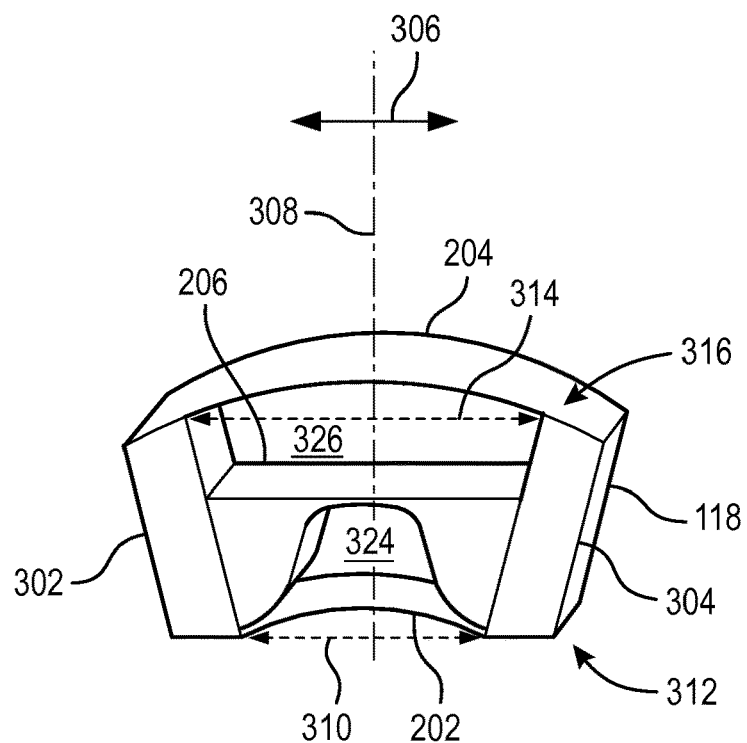
FIG. 3 schematically illustrates an example of the interferometer grating support.
Figure 4:
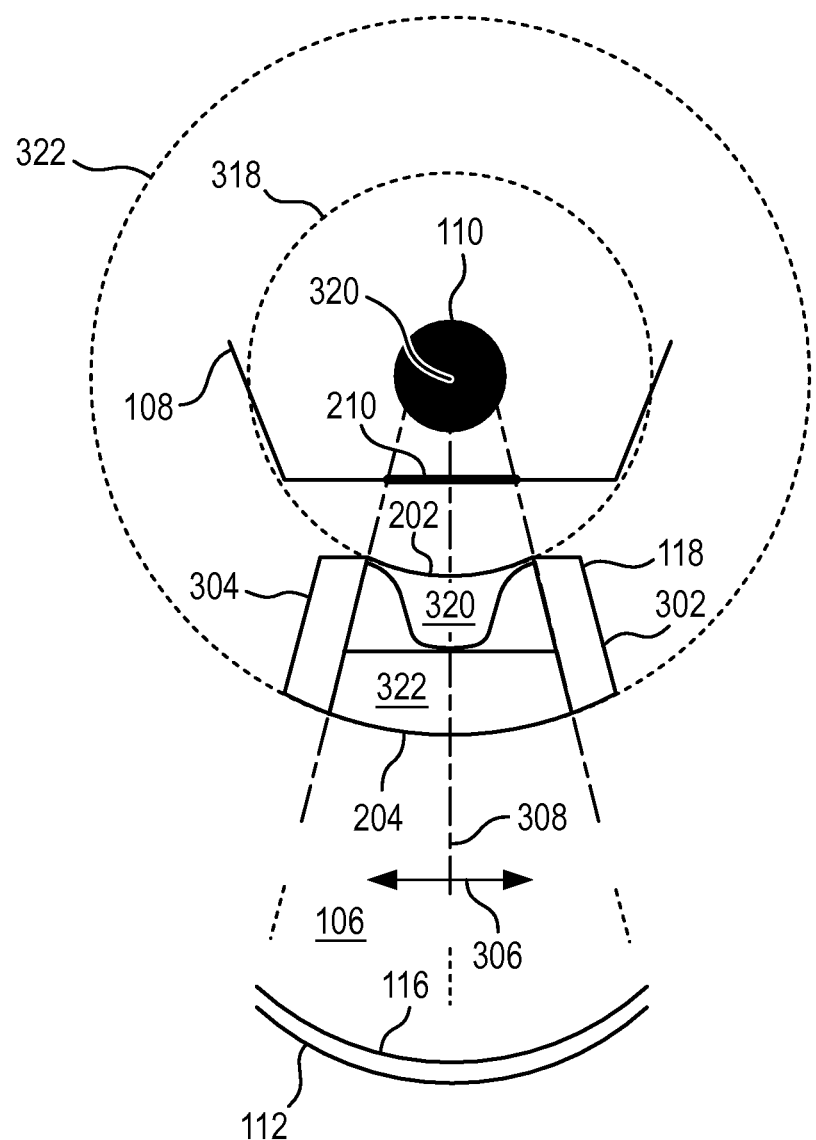
FIG. 4 schematically illustrates an example interferometer grating support in connection with the radiation source and detector array.

FIGS. 3 and 4 schematically illustrates a non-limiting example of the grating support 118. FIG. 3 schematically illustrates the grating support 118 by itself, and FIG. 4 schematically illustrates the grating support 118 in connection with the radiation source 108, the G2 grating 116, and the detector array 112. The relative size and/or location of the components are not limiting and are provided for explanatory purposes.

The grating support 118 includes at least two elongate supports 302 and 304 that are separated from each other in a direction 306, which is transverse to a vertical line 308 from a center of the focal spot 110 to the detector array 112, by a non-zero distance at least equal to a length of the bowtie filter 206. The at least two supports 302 and 304 are symmetrically disposed about the vertical line 308 and taper. The non-zero distance varies from a distance 310 at an end 312 of the grating support 118 which is disposed adjacent the nearer the focal spot 110 to a distance 314 at an opposing end 316 of the grating support 118, which is farther from the focal spot 110. The non-zero distance varies linearly. In a variation, the non-zero distance varies non-linearly. The non-zero distance is at least large enough so that the bowtie filter 206 fits there between. The illustrated size and shape of the at least two supports 302 and 304 is not limiting.

The G0 grating 202 is coupled at the end 312 of the grating support 118. The G0 grating 202 can be coupled thereto via a fastener such as an adhesive (e.g., glue), a screw, a rivet, a clamp, and the like. In this embodiment, the G0 grating 202 is arc shaped and follows a circle 318 having a center or midpoint 320 at a center of the focal spot 110. The G1 grating 204 is coupled to the opposing end 316 of the grating support 118. Likewise, the G1 grating 204 can be coupled via a fastener such as an adhesive (e.g., glue), a screw, a rivet, a clamp, and the like. In this embodiment, the G1 grating 204 is also arc shaped and follows a circle 322 (which is concentric to the circle 318) sharing the center or midpoint 320. The G0 and G1 gratings 202 and 204 can be pre-formed with the arc shape and/or bent during installation on the at least two supports 302 and 304.

In this embodiment, the G0 and G1 gratings 202 and 204 are separated from each other along the line 308 by a distance of ten centimeters (10 cm). In a variation, this distance is twenty centimeters (20 cm). In a variation, this distance is value between eight and thirty centimeters (8-30 cm). Generally, the separation corresponds to the Talbot distance. In one instance, this distance is static. In another instance, this distance is variable and can be manually and/or automatically adjusted. The grating support 118 includes a material with a temperature expansion coefficient such that the G0 and G1 gratings 202 and 204 maintain their positions. A suitable material is a nickel-iron alloy having a low coefficient of thermal expansion such as Invar®, a product of Imphy Alloys, France, and/or product. Furthermore, the grating support 118 can maintain the suitable positions under centrifugal forces of a CT scanner (e.g., 2 g to 6 g, 4 g, etc.).

A volume 324 bound by the G0 grating 202 and the bow-tie filter 206 is free of any x-ray attenuating material. A volume 326 bound by the G1 grating 204, the at least two supports 302 and 304, and the bow-tie filter 206 is also free of any x-ray attenuating material. A suitable bow-tie filter 206 includes a conventional bowtie filter that combines strong attenuation areas with reduced beam hardening. In one instance, this includes a bowtie filter that is relatively thick such as seven centimeters (7 cm) of a low Z material such as Teflon®, a product of Chemours, USA. In another embodiment, the bowtie filter may be made of a different material and/or have a different thickness. In yet another instance, the bowtie filter 206 is omitted. The bowtie filter 206 can be part of an assembled grating support 118 and/or installable therein.

Figure 5:
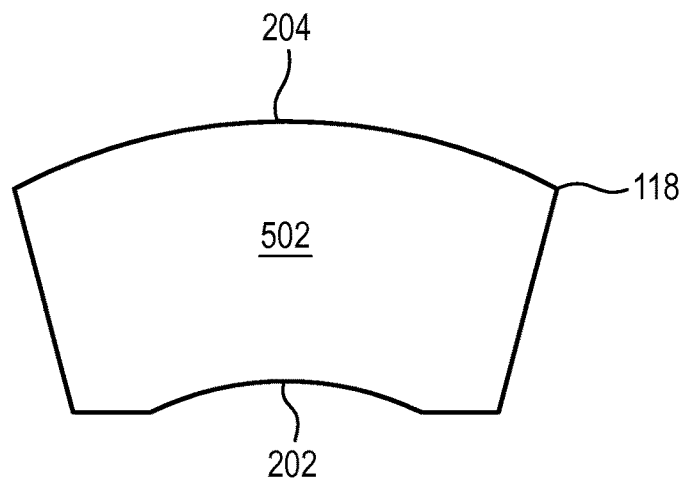
FIG. 5 schematically illustrates another example interferometer grating support.
Figure 6:
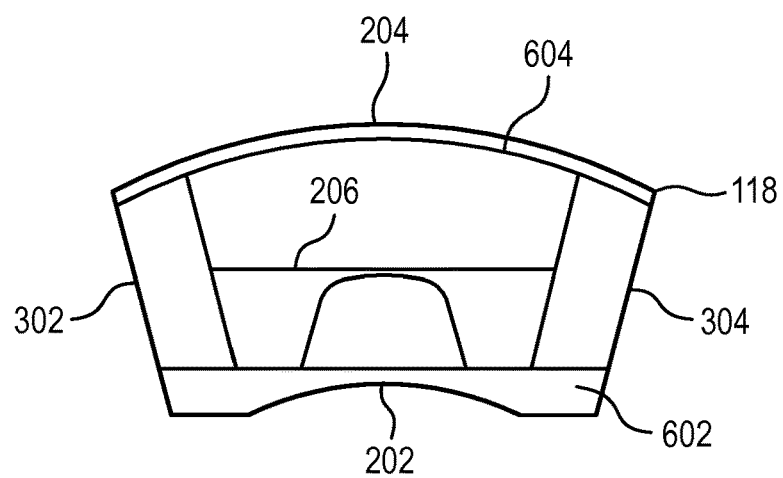
FIG. 6 schematically illustrates yet another example interferometer grating support.
Figure 7:
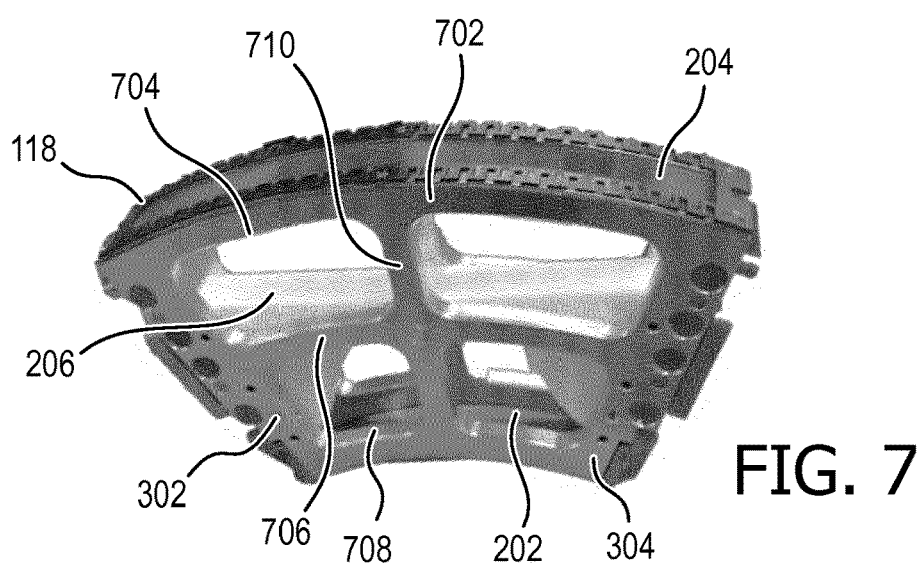
FIG. 7 schematically illustrates still another example interferometer grating support.

FIGS. 5, 6 and 7 illustrate non-limiting variations of the grating support 118.

The grating support 118 in FIG. 5 is substantially similar to the grating support 118 in FIGS. 3 and 4, except that the grating support 118 in FIG. 5 includes at least one wall 502. The illustrated wall 502 is shaped to follow a perimeter of the G0 and G1 gratings 202 and 204 and the at least two supports 302 and 304. In other embodiments, the wall 502 is otherwise shaped. Furthermore, the grating support 118 can include the wall 502 on only one side of the grating support 118 or on both side of the grating support 118. Furthermore, the wall 502 shape does not have to follow the perimeter of the G0 and G1 gratings 202 and 204 and the at least two supports 302 and 304. For example, in a variation, the wall 502 is rectangular.

The grating support 118 in FIG. 6 is substantially similar to the grating support 118 in FIGS. 3 and 4, except that the grating support 118 in FIG. 6 includes support members 602 and 604, with the member 602 at and along the G0 grating 202 and the member 604 at and along the G1 grating 204. In another embodiment, the grating support 118 can include more or less support members. In one instance, at least one of the support members 602 and 604 facilitates holding the G0 or G1 gratings 202 and 204 in place. In another embodiment, at least one of the support members 602 and 604 does not facilitate holding the G0 or G1 gratings 202 and 204 in place.

The grating support 118 in FIG. 7 is substantially similar to the grating support 118 in FIGS. 3 and 4, except that with the grating support 118 in FIG. 7 the at least two supports 302 and 304 are part of a single support 702, which includes top, middle and bottom legs 704, 706 and 708, all extending between the at least two supports 302 and 304, and another support 710, extending like the at least two supports 302 and 304 from the top leg 704 through the intermediate leg 706 to the bottom leg 708. In another embodiment, the grating support 118 can include a combination of the FIGS. 3-7 and/or another configuration(s).

Figure 8:
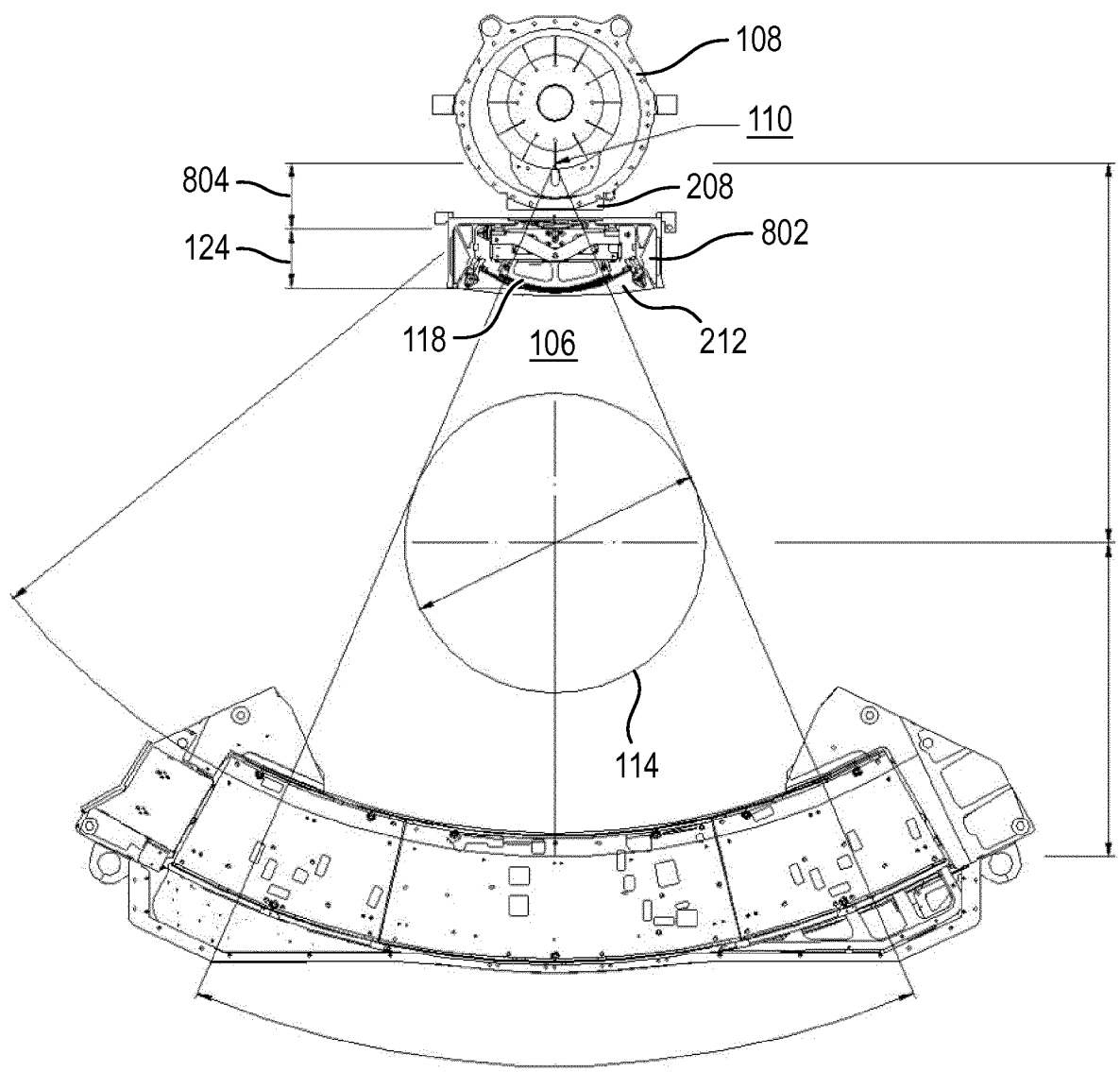
FIG. 8 schematically illustrates the interferometer grating support supported in an example support bracket in the system.

FIG. 8 illustrates embodiment in which the grating support 118 is supported in the system 100 by a bracket 802. In this example, the bracket 802 supports the grating support 118 at a static position. The bracket 802 also supports the low energy x-ray photon filter 208 and the beam collimator 212. In a variation, at least one of the low energy x-ray photon filter 208 and the beam collimator 212 is alternatively supported by a component other than the bracket 802. A distance 804 is between the focal spot 110 and the G0 grating 202 (no visible).

In one instance, the grating support 118 is releasably affixed to the bracket 802 and can be readily removed therefrom, e.g., to replace the grating support 118 and/or a component thereof (e.g., the bowtie filter 206). In another instance, the bracket 802 is releasably affixed in the system 100 and can be readily removed therefrom, e.g., to replace the bracket 802 and/or a component thereof (e.g., the grating support 118). The bracket 802 can be affixed to the source 108 and/or the rotating gantry 104 (FIG. 1). FIG. 8 also shows the distance 214 between the G0 grating 202 and the G1 grating 204.

Figure 9:
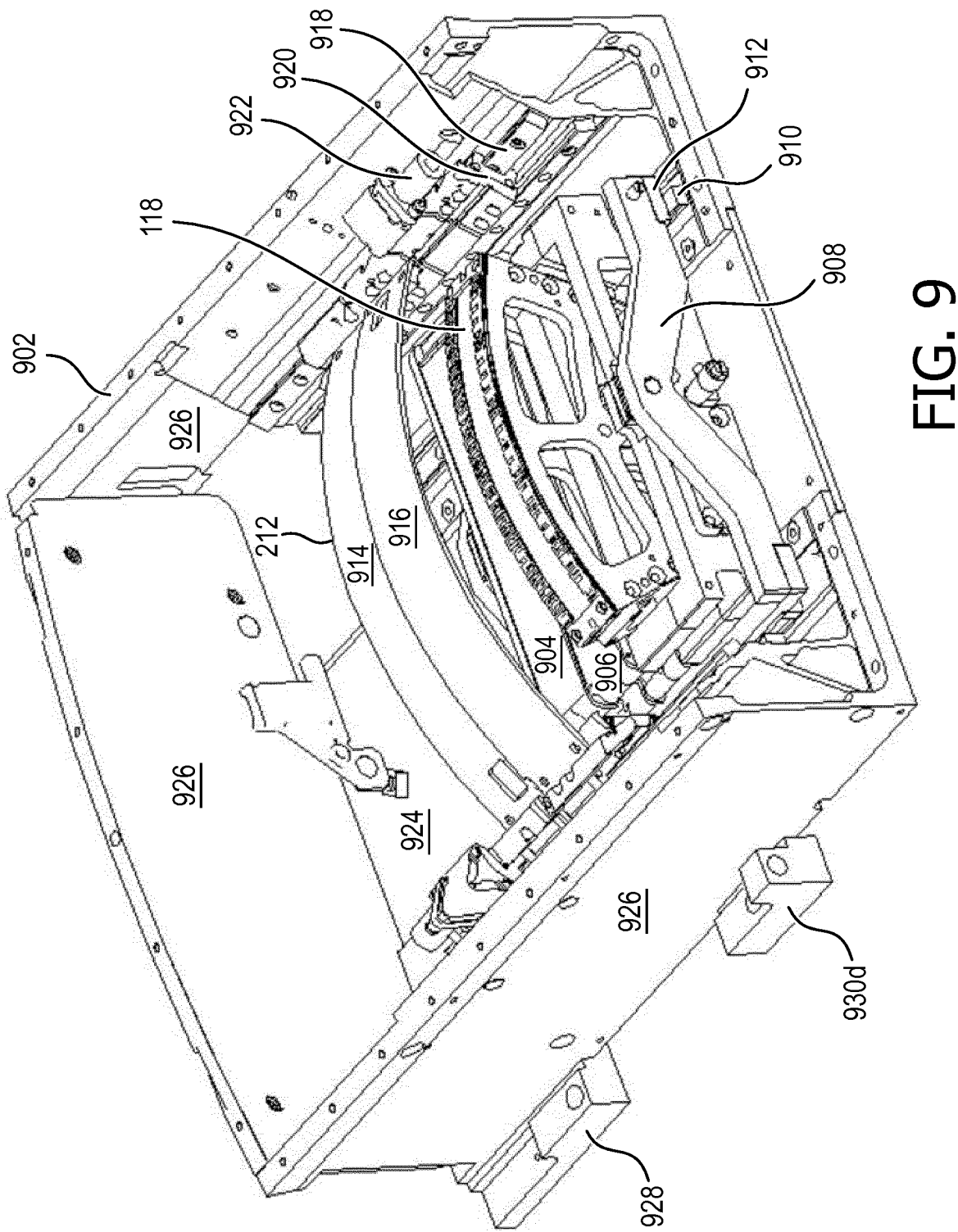
FIG. 9 schematically illustrates the interferometer grating support in connection with another example support bracket.

FIG. 9 illustrates an alternative support bracket 902. The alternative support bracket 902 is configured to support the grating support 118 and one or more alternative x-ray beam conditioners such as bowtie filters 904 and 906. In this example, the bowtie filters 904 and 906 have different geometry corresponding to different size, shape, etc. objects and/or subjects. In a variation, the support bracket 902 is configured to support more or less and/or other x-ray beam conditioning components.

The grating support 118 and the bowtie filters 904 and 906 are affixed in an assembly 908. The assembly 908 is translatably coupled to at least one rail 910 via at least one bearing 912. A controller (not visible) controls a motor (not visible) to drive a drive system (not visible) such as a lead screw, ball screw, gear(s), chain, etc. to translate the assembly 908 to move at least between: 1) a position (shown) in which the bowtie filter 904 is between blades 914 of the collimator 212 and the low energy photon filer 208 (not visible); 2) a position in which the bowtie filter 906 is between the blades 914 and 916 of the collimator 212 and the low energy photon filer 208, and 3) a position in which the grating support 118 is between blades 914 of the collimator 212 and the low energy photon filer 208.

The particular one of the alternative x-ray beam conditioners positioned between the blades 914 of the collimator 212 and the low energy photon filer 208 depends on the particular scan to be performed. For example, where a grating-based x-ray imaging scan is to be performed, which can be selected at the console 126 (FIG. 1) during scan planning for a subject, the console 126 transmits a signal that causes the controller to control the motor to drive the drive system to translate the assembly 908 to position the grating support 118 between the blades 914 of the collimator 212 and the low energy photon filer 208. For a non-grating-based x-ray imaging scan (or conventional scan), the console 126 transmits a signal that causes the controller to control the motor to drive the drive system to translate the assembly 908 to position the bowtie filter 904 or 96 between the blades 914 of the collimator 212 and the low energy photon filer 208.

The blades 914 and 916 of the collimator 212 are translatably affixed to at least one other rail 918 via at least one bearing 920. A controller (not visible) controls a motor 922 to drive a drive system (not visible) such as a lead screw, ball screw, gear(s), chain, etc. to translate the blades 914 and 916. The blades 914 and 916 of the collimator 212, in one instance, move to a first position where the blades 914 and 916 contact each other and block x-rays from passing to the examination region 106 (FIG. 1). The blades 914 and 916 of the collimator 212, in another instance, move away from each other alternatively to one of a plurality of predetermined positions, each corresponding to a different distance between the blades 914 and 916 and a different beam width. The blades 914 and 916 of the collimator 212 can also be moved together in coordination in a same direction.

In one instance, at least the grating support 118 is releasably affixed to the support bracket 902 and can be readily removed therefrom, e.g., to replace the grating support 118 and/or a component thereof (e.g., the bowtie filter 206). Additionally or alternatively, at least one of the collimator 212 and/or the low energy photon filer 208 is releasably affixed to the bracket 902 and can be readily removed therefrom, e.g., to replace the collimator 212 and/or the low energy photon filer 208. Additionally or alternatively, the bracket 902 is releasably affixed in the system 100 and can be readily removed therefrom, e.g., to replace the bracket 902 and/or a component supported thereby.

The illustrated support bracket 902 is shaped similar to a box with a bottom 924, four sides 926 (a front side is rendered transparent so that the grating support 118 and other components can be seen), and a top (which is rendered transparent so that the grating support 118 and other components can be seen). This configuration is non-limiting, and other structural configurations, such as non-box shaped, are contemplated herein. The illustrated support bracket 902 also includes mounting members 928 and 930. The bracket 902 can be affixed to the source 108 and/or the rotating gantry 104 (FIG. 1). Other mounting members are contemplated herein.

For a configuration in which the system 100 is configured with the support bracket 902, the G2 grating 120 is configured to move in the beam path between the examination region 106 and the detector array 112 and out of the beam path between the examination region 106 and the detector array 112. For example, for a grating-based x-ray imaging scan, the G2 grating 120 is moved into a region between the examination region 106 and the detector array 112 and in the beam path, and for a conventional CT scan, the G2 grating 120 is moved out the region between the examination region 106 and the detector array 112 and one of the bowtie filters 904 or 906 is moved into the region between the examination region 106 and the detector array 112 and in the beam path. The G2 grating 120 can be moved via an electro-mechanical system, which may include a controller, a motor, a drive system, and/or other components.

Figure 10:
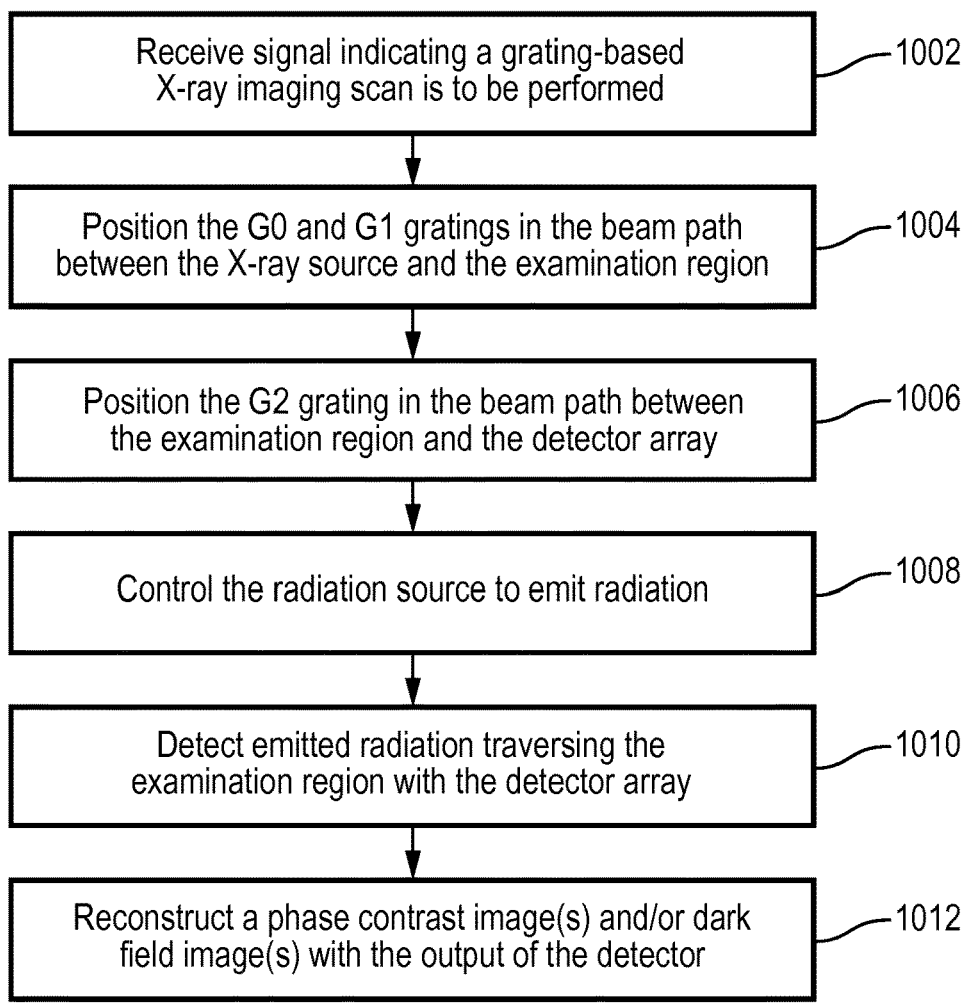
FIG. 10 illustrates an example method in accordance with an embodiment herein.

FIG. 10 illustrates an example method in accordance with an embodiment described herein.

It is to be appreciated that the ordering of the acts is not limiting. As such, other orderings are contemplated herein. In addition, one or more acts may be omitted and/or one or more additional acts may be included.

At 1002, an input signal indicating a grating-based x-ray imaging scan is to be performed is received at the console 126 of the imaging system 100.

At 1004, the grating support 118, which includes the gratings G0 and G1 202 and 204 and the bowtie filter 206, is positioned between the low energy photon filter 208 and the collimator 212, via electro-mechanical control.

At 1006, the grating G2 116 is positioned between the examination region 106 and the detector array 112.

At 1008, a radiation source 108 is controlled to emit x-ray radiation.

At 1010, a detector array 112 is controlled, in coordination with the control of the radiation source 108, to detect emitted x-ray radiation traversing the examination region 106 and generate a signal indicative thereof.

At 1012, the signal is reconstructed to generate a phase contrast image(s) and/or a dark field image(s).

Figure 11:
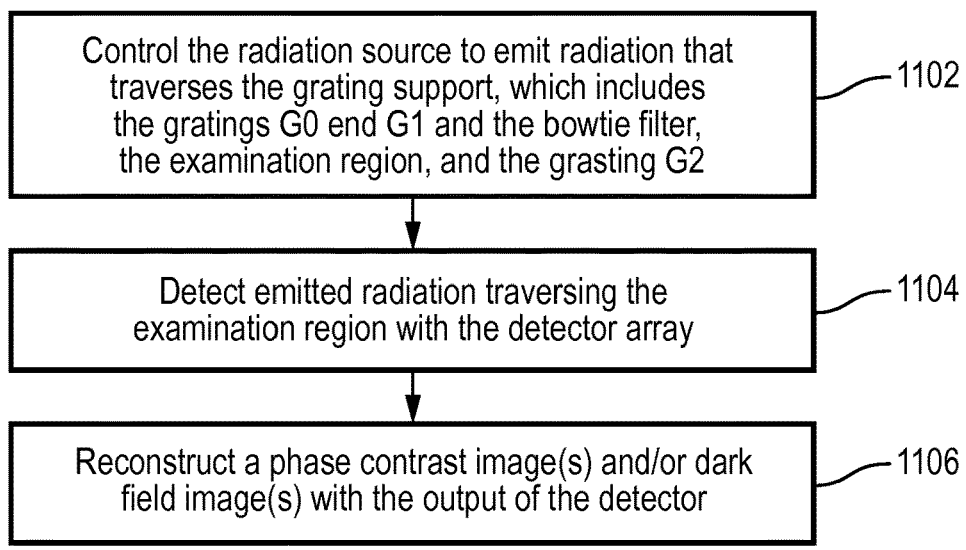
FIG. 11 illustrates another example method in accordance with an embodiment herein.

FIG. 11 illustrates an example method in accordance with an embodiment described herein.

It is to be appreciated that the ordering of the acts is not limiting. As such, other orderings are contemplated herein. In addition, one or more acts may be omitted and/or one or more additional acts may be included.

At 1102, a radiation source 108 is controlled to emit x-ray radiation, which traverses the grating support 118, which includes the gratings G0 and G1 202 and 204 and the bowtie filter 206, the examination region 106, and the grating G2 116.

At 1104, a detector array 112 is controlled to detect emitted x-ray radiation traversing the examination region 106 and generate a signal indicative thereof.

At 1106, the signal is reconstructed to generate a phase contrast image(s) and/or a dark field image(s).

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium, which is not computer readable storage medium.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An interferometer grating support of an imaging system configured for grating-based x-ray imaging, comprising:
   at least two elongate supports separated from each other by a non-zero distance, wherein the at least two elongate supports have a first end and a second end;
   a first arc shaped grating affixed to the first end of the at least two elongate supports; and
   a second arc shaped grating affixed to the second end of the at least two elongate supports;
   wherein the first arc shaped grating includes a source grating of an interferometer and the second arc shaped grating includes a phase or absorber grating of the interferometer.

2. The grating support of claim 1, further comprising:
a bowtie filter disposed between the at least two elongate supports, the first arc shaped grating, and the second arc shaped grating.

3. The grating support of claim 1, wherein a distance between the first arc shaped grating and the second arc shaped grating is a value between eight and thirty centimeters.

4. The grating support of claim 1, wherein a distance between the first arc shaped grating and the second arc shaped grating is on an order of ten or twenty centimeters.

5. The grating support of claim 1, wherein a first arc of the first arc shaped grating and a second arc of the second arc shaped grating follow perimeters of concentric circles with a center point corresponding to a focal spot location in the system.

6. The grating support of claim 1, wherein the at least two elongate supports taper from the second arc shaped grating to the first arc shaped grating and are symmetric about a vertical line through a center of the at least two elongate supports.

7. An imaging system configured for grating-based x-ray imaging, comprising:
a gantry;
a radiation source located at the gantry;
a detector array disposed across an examination region from the radiation source;
a grating support disposed between the radiation source and the examination region; and
an interferometer, including:
a first arc shaped source grating;
a second arc shaped phase grating, wherein the grating support supports the first arc shaped source grating and the second arc shaped phase grating; and
an absorber grating disposed between the examination region and the detector array.

8. The imaging system of claim 7, further comprising:
a support bracket configured to support only the grating support.

9. The imaging system of claim 7, further comprising:
a support bracket configured to support the grating support and at least one other beam conditioning component.

10. The imaging system of claim 9, further comprising:
a sub-system configured to move the support bracket within the sub-system to position the grating support or the at least one other beam conditioning component in a path of an x-ray beam.

11. The imaging system of claim 9, further comprising:
a low energy photon filter disposed between the radiation source and the first arc shaped source grating, wherein the grating support supports the low energy photon filter.

12. The imaging system of claim 9, further comprising:
a beam collimator disposed between the second arc shaped phase grating and the examination region, wherein the grating support supports the beam collimator.

13. The imaging system of claim 7, further comprising:
a low energy photon filter disposed between the radiation source and the first arc shaped source grating.

14. The imaging system of claim 7, further comprising:
a beam collimator disposed between the second arc shaped phase grating and the examination region.

15. The imaging system of claim 7, further comprising:
a bowtie filter between the first arc shaped source grating and the second arc shaped phase grating.

16. The imaging system of claim 15, wherein the grating support includes:
at least two elongate supports separated from each other by a non-zero distance, wherein the first arc shaped source grating is affixed to a first end of the at least two elongate supports, the second arc shaped phased grating is affixed to a second end of the at least two elongate supports, and the bowtie filter is disposed between the at least two elongate supports, the first arc shaped source grating, and the at second arc shaped phase grating.

17. The imaging system of claim 16, wherein a distance between the at least two elongate supports at the first end is less than a distance between the at least two elongate supports at the second end.

18. A non-transitory computer readable medium configured with computer executable instructions which when executed by a processor cause the processor to:
move a grating support configured to support source and phase gratings of an interferometer and a bowtie filter into a region between a low energy photon filter and a beam collimator located between a radiation source and an examination region for a grating-based x-ray imaging scan.

19. The non-transitory computer readable medium of claim 18, wherein the instructions further cause the processor to:
control the radiation source to emit x-ray radiation;
control a detector array to detect the emitted x-ray radiation and generate a signal indicative thereof; and
control a reconstructor to reconstruct the signal and generate a phase contrast image.

20. The non-transitory computer readable medium of claim 18, wherein the instructions further cause the processor to:
move the grating support out of the region between the low energy photon filter and the beam collimator; and
move a different beam conditioning component into the region between the low energy photon filter and the beam collimator for a conventional scan.

21. The non-transitory computer readable medium of claim 20, wherein the instructions further cause the processor to:
control the radiation source to emit x-ray radiation;
control a detector array to detect the emitted x-ray radiation and generate a signal indicative thereof; and
control a reconstructor to reconstruct the signal and generate a conventional image.

* * * * *